(12) United States Patent
Lee et al.

(10) Patent No.: US 10,233,265 B2
(45) Date of Patent: Mar. 19, 2019

(54) MODIFIED CONJUGATED DIENE POLYMER AND METHOD FOR PREPARING THE SAME

(71) Applicant: LG CHEM, LTD., Seoul (KR)

(72) Inventors: Ro Mi Lee, Daejeon (KR); Sang Mi Lee, Daejeon (KR); Choon Hwa Lee, Daejeon (KR); Byung Hoon Yoon, Daejeon (KR); Jin Young Kim, Daejeon (KR); Moon Seok Chun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 316 days.

(21) Appl. No.: 15/357,734

(22) Filed: Nov. 21, 2016

(65) Prior Publication Data

US 2017/0066850 A1  Mar. 9, 2017

Related U.S. Application Data

(62) Division of application No. 14/349,478, filed as application No. PCT/KR2013/000892 on Feb. 4, 2013, now Pat. No. 9,540,472.

(30) Foreign Application Priority Data

Feb. 6, 2012  (KR) .................. 10-2012-0011617
Jan. 31, 2013  (KR) .................. 10-2013-0011063

(51) Int. Cl.
C07F 7/00  (2006.01)
C08C 19/44  (2006.01)
C08K 3/36  (2006.01)
C08C 19/25  (2006.01)
C08F 236/10  (2006.01)
C07F 7/18  (2006.01)
C08K 3/04  (2006.01)
C08K 5/54  (2006.01)

(52) U.S. Cl.
CPC ............ *C08C 19/25* (2013.01); *C07F 7/1804* (2013.01); *C08C 19/44* (2013.01); *C08F 236/10* (2013.01); *C08K 3/04* (2013.01); *C08K 3/36* (2013.01); *C08K 5/5406* (2013.01)

(58) Field of Classification Search
CPC ............ C07F 7/184; C08C 19/44; C08K 3/36
USPC .......................................... 525/102; 556/413
See application file for complete search history.

(56) References Cited

U.S. PATENT DOCUMENTS

2013/0023623 A1* 1/2013 Nakamura ................ B60C 1/00
524/572

FOREIGN PATENT DOCUMENTS

| EP | 2184318 A2 | 5/2010 |
|---|---|---|
| JP | 2005290355 A | 10/2005 |
| JP | 2006-285558 A | 11/2008 |
| JP | 2010-111753 A | 5/2010 |
| JP | 2010-116546 A | 5/2010 |
| JP | 2011-116823 A | 6/2011 |
| JP | 2012-224768 A | 11/2012 |
| TW | 201144328 A | 12/2011 |
| WO | 2007114203 A1 | 10/2007 |
| WO | 2011-125698 A1 | 10/2011 |
| WO | 2011125698 A1 | 10/2011 |
| WO | 2011129425 A1 | 10/2011 |
| WO | 2011/155326 A1 | 12/2011 |

* cited by examiner

Primary Examiner — Kelechi C Egwim
(74) Attorney, Agent, or Firm — Dentons US LLP

(57) ABSTRACT

Disclosed are a modified conjugated diene polymer and a method for preparing the same. The modified conjugated diene polymer and the method for preparing the same advantageously provide superior compatibility with an inorganic filler, heat generation, tensile strength and abrasion resistance, low fuel consumption and excellent resistance on wet roads.

10 Claims, No Drawings

MODIFIED CONJUGATED DIENE POLYMER AND METHOD FOR PREPARING THE SAME

This application is a divisional of U.S. application Ser. No. 14/349,478, filed Apr. 3, 2014, now allowed, which is a National Stage Application of International Application No. PCT/KR2013/000892, filed Feb. 4, 2013, and claims priority to and the benefit of Korean Patent Application No. 10-2012-0011617, filed on Feb. 6, 2012, and Korean Patent Application No. 10-2013-0011063, filed on Jan. 31, 2013, the disclosures of which are incorporated herein by reference in their entirety.

TECHNICAL FIELD

The present invention relates to a modified conjugated diene polymer and a method for preparing the same. The present invention relates to a modified conjugated diene polymer which exhibits superior compatibility with an inorganic filler, heat generation, tensile strength and abrasion resistance, low fuel consumption and excellent resistance on wet roads and a method for preparing the same.

BACKGROUND ART

Demands for stability, durability and low fuel consumption of vehicles are increasing. Accordingly, there is an increasing demand for rubbers exhibiting excellent resistance on wet roads and mechanical strength and low rolling resistance as materials for vehicle tires, in particular, tire treads contacting the road.

Conventional tire treads have been produced using a conjugated diene rubber mixed with an inorganic filler in order to reinforce the properties described above, but have problems of great hysteresis loss or low dispersibility.

DISCLOSURE

Technical Problem

Therefore, the present invention has been made in view of the above problems, and it is one object of the present invention to provide a modified conjugated diene polymer which exhibits superior compatibility with an inorganic filler, heat generation, tensile strength and abrasion resistance, low fuel consumption and excellent resistance on wet roads, and a method for preparing the same.

It is another object of the present invention to provide a rubber composition comprising the modified conjugated diene polymer and a tire comprising the rubber composition.

It is yet another object of the present invention to provide a modifying agent used for preparation of the modified conjugated diene polymer.

The objects and other objects can be accomplished by the present invention described below.

Technical Solution

In accordance with one aspect of the present invention, provided is a modified conjugated diene polymer represented by the following Formula 1:

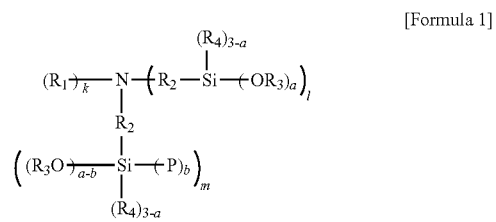

[Formula 1]

wherein $R_1$ is an alkyl group or an alkylsilyl group, $R_2$ is an alkyl group or an alkylene group, $R_3$ and $R_4$ are an alkyl group, a is an integer of 1 to 3, l and k are an integer of 0 to 2, m is an integer of 1 to 3, l+k+m satisfy 3, p is a conjugated diene polymer chain, and b is an integer of 1 to 3, wherein two $R_1$ bonded to nitrogen, when k is 2, may be identical or different, and in the same way, when l and m are 2 or more, the relevant groups may be identical or different.

In accordance with another aspect of the present invention, provided is a method for preparing a modified conjugated diene polymer comprising (a) polymerizing a conjugated diene monomer, or a conjugated diene monomer and an aromatic vinyl monomer in the presence of a solvent using an organometallic compound to prepare an active polymer having a metal end group, and (b) adding a compound represented by the following Formula 2 to the active polymer to modify the active polymer:

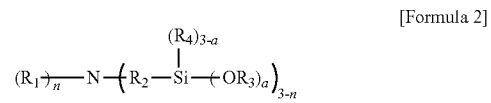

[Formula 2]

wherein $R_1$ is an alkyl group or an alkylsilyl group, $R_2$ is an alkyl group or an alkylene group, $R_3$ and $R_4$ are an alkyl group, a is an integer of 1 to 3, and n is an integer of 0 to 2, wherein two $R_1$ bonded to nitrogen may be identical or different when n is 2, and in the same way, when 3-n is 2 or more, the relevant groups may be identical or different.

In accordance with another aspect of the present invention, provided is a modified conjugated diene polymer rubber composition comprising 0.1 to 200 parts by weight of an inorganic filler with respect to 100 parts by weight of the modified conjugated diene polymer.

In accordance with another aspect of the present invention, provided is a tire comprising the modified conjugated diene polymer rubber composition.

In accordance with yet another aspect of the present invention, provided is a modifying agent used for preparation of the modified conjugated diene polymer.

Advantageous Effects

As apparent from the fore-going, the present invention advantageously provides a modified conjugated diene polymer which exhibits superior compatibility with an inorganic filler, heat generation, tensile strength and abrasion resistance, low fuel consumption and excellent resistance on wet roads, and a method for preparing the same.

BEST MODE

Hereinafter, the modified conjugated diene polymer, the method for preparing the same, the rubber composition comprising the modified conjugated diene polymer and the tire comprising the rubber composition will be described in detail.

The modified conjugated diene polymer according to the present invention comprises a polymer represented by the following Formula 1:

$$(R_1)_k-N-(R_2-\underset{\underset{(R_4)_{3-a}}{|}}{Si}-(OR_3)_a)_l$$
$$\underset{R_2}{|}$$
$$((R_3O)_{a-b}-\underset{\underset{(R_4)_{3-a}}{|}}{Si}-(P)_b)_m$$

[Formula 1]

wherein $R_1$ is an alkyl group or an alkylsilyl group, $R_2$ is an alkyl group or alkylene group, $R_3$ and $R_4$ are an alkyl group, a is an integer of 1 to 3, l and k are an integer of 0 to 2, m is an integer of 1 to 3, l+k+m satisfy 3, p is a conjugated diene polymer chain, and b is an integer of 1 to 3, wherein two $R_1$ bonded to nitrogen, when k is 2, may be identical or different, and similarly, corresponding groups, when l and m are 2 or more, may be identical or different.

$R_1$ is for example a C1-C12 alkyl group or a C1-C12 alkylsilyl group.

$R_2$ is for example a C1-C12 alkyl group or a C1-C12 alkylene group.

$R_3$ and $R_4$ are for example a C1-C12 alkyl group.

l is for example 0 or 1.

k is for example 0 or 1. Within this range, there are advantages in that hysteresis loss is reduced, and compatibility with an inorganic filler, in particular, silica is excellent.

m is for example 1 or 2 and, in another example, m is 2 or 3.

The total number of p is 1 to 9, 1 to 5, or 1 to 3. Within this range, there is an advantage in that produced tires exhibit superior resistance on wet roads and low fuel consumption.

In Formula 1, for example, k is 1, l is 0, and m is 2.

In Formula 1, in another example, k is 1, l is 1, and m is 1.

The conjugated diene polymer chain is for example a chain comprising a conjugated diene monomer alone, or the conjugated diene monomer and an aromatic vinyl monomer.

In another example, the conjugated diene polymer chain may be a polymer chain comprising 0.0001 to 40% by weight, 10 to 35% by weight or 20 to 30% by weight of the aromatic vinyl monomer, based on 100% by weight in total of the conjugated diene monomer and the aromatic vinyl monomer.

The polymer chain comprising the conjugated diene monomer and the aromatic vinyl monomer may be for example a random polymer chain.

The conjugated diene monomer is for example selected from the group consisting of 1,3-butadiene, 2,3-dimethyl-1,3-butadiene, piperylene, 3-butyl-1,3-octadiene, isoprene, 2-phenyl-1,3-butadiene and mixtures thereof.

The aromatic vinyl monomer is for example selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, 1-vinyl-5-hexylnaphthalene and mixtures thereof. In another example, the aromatic vinyl monomer is styrene or α-methylstyrene.

The modified conjugated diene polymer, for example, has a Mooney viscosity of 40 or higher, or 40 to 90.

In another example, the modified conjugated diene polymer may have a Mooney viscosity of 45 to 85, or 50 to 80.

The modified conjugated diene polymer, for example has a number average molecular weight of 1,000 to 2,000,000 g/mol, 10,000 to 1,000,000 g/mol, or 100,000 to 500,000 g/mol.

The conjugated diene polymer, for example, has a vinyl content of 18% or higher, 25% or higher, 30 to 70%, or 40 to 60%. Within this range, there are advantages in that glass transition temperature of polymer is increased, properties such as running resistance and brake power, required for produced tires are satisfied and fuel consumption is reduced.

The vinyl content means a content of a unit having a vinyl group, or a content of a 1,2-added conjugated diene monomer rather than a 1,4-added conjugated diene monomer with respect to 100% by weight of the conjugated diene monomer.

The modified conjugated diene polymer may for example have a PDI of 0.5 to 10, 0.5 to 5, or 1.0 to 2.0.

Regarding viscoelasticity, the modified conjugated diene polymer for example has a Tan δ at 0° C., measured at 10 Hz using DMA after mixing with silica, of 0.6 to 1 or 0.9 to 1. Within this range, resistance on road or wet road is greatly improved, as compared to the prior art.

In addition, the modified conjugated diene polymer has, for example, a Tan δ at 60° C., of 0.06 to 0.09, or 0.07 to 0.08. Within this range, rolling resistance or rotational resistance (RR) is advantageously greatly improved.

The method for preparing a modified conjugated diene polymer according to the present invention includes (a) polymerizing a conjugated diene monomer, or a conjugated diene monomer and an aromatic vinyl monomer in the presence of a solvent using an organometallic compound to prepare an active polymer having a metal end group, and (b) adding a compound represented by the following Formula 2 to the active polymer to modify the active polymer:

$$(R_1)_n-N-(R_2-\underset{\underset{(R_4)_{3-a}}{|}}{Si}-(OR_3)_a)_{3-n}$$

[Formula 2]

wherein $R_1$ is an alkyl group or an alkylsilyl group, $R_2$ is an alkyl group or an alkylene group, $R_3$ and $R_4$ are an alkyl group, a is an integer of 1 to 3, and n is an integer of 0 to 2, wherein two $R_1$ bonded to nitrogen may be identical or different when n is 2, and similarly, corresponding groups may be identical or different when 3-n is 2 or more.

n is for example 0 or 1.

$R_1$ to $R_4$ have been defined in above.

The conjugated diene monomer is for example selected from the group consisting of 1,3-butadiene, 2,3-dimethyl-1,3-butadiene, piperylene, 3-butyl-1,3-octadiene, isoprene, 2-phenyl-1,3-butadiene and mixtures thereof.

The aromatic vinyl monomer is for example selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, 1-vinyl-5-hexylnaphthalene and mixtures thereof. In another example, the aromatic vinyl monomer is styrene or α-methylstyrene.

The aromatic vinyl monomer may be present in an amount of 0.0001 to 40% by weight, 10 to 35% by weight or 20 to 30% by weight, based on 100% by weight in total of the conjugated diene monomer and the aromatic vinyl monomer.

The solvent may for example comprise at least one selected from the group consisting of hydrocarbons, n-pentane, n-hexane, n-heptane, isooctane, cyclohexane, toluene, benzene and xylene.

The organometallic compound may for example comprise at least one selected from the group consisting of organic alkali metal compounds, organolithium compounds, organosodium compounds, organopotassium compounds, organorubidium compounds and organocesium compounds.

In another example, the organometallic compound may comprise at least one selected from the group consisting of methyl lithium, ethyl lithium, isopropyl lithium, n-butyl lithium, sec-butyl lithium, tert-butyl lithium, n-decyl lithium, tert-octyl lithium, phenyl lithium, 1-naphthyl lithium, n-eicosyl lithium, 4-butylphenyl lithium, 4-tolyl lithium, cyclohexyl lithium, 3,5-di-n-heptylcyclohexyl lithium and 4-cyclopentyl lithium.

In another example, the organometallic compound is n-butyl lithium, sec-butyl lithium or a mixture thereof.

In another example, the organometallic compound may comprise at least one selected from the group consisting of sodium naphthyl, potassium naphthyl, lithium alkoxide, sodium alkoxide, potassium alkoxide, lithium sulfonate, sodium sulfonate, potassium sulfonate, lithium amide, sodium amide and potassium amide. The organometallic compound may be used in combination with another organometallic compound.

The organometallic compound is for example used in an amount of 0.01 to 10 mmol, 0.05 to 5 mmol, 0.1 to 2 mmol or 0.1 to 1 mmol, based on 100 g in total of the monomer.

A molar ratio of the organometallic compound to the compound represented by Formula 2 is for example 1:0.1 to 1:10, or 1:0.5 to 1:2.

The active polymer having a metal end group means a polymer wherein a polymer anion is bonded to a metal cation.

The method for preparing a modified conjugated diene polymer according to the present invention, for example, comprises further adding a polar additive during (a) the polymerization.

The polar additive is for example a base. In another example, the polar additive is ether, amine or a mixture thereof, or is selected from the group consisting of tetrahydrofuran, ditetrahydrofurfurylpropane, diethylether, cycloamylether, dipropyl ether, ethylmethylether, diethylene glycol, dimethyl ether, tertiary butoxyethoxyethane bis(2-dimethylaminoethyl)ether, (dimethylaminoethyl) ethylether, trimethylamine, triethylamine, tripropylamine, and tetramethylethylenediamine. In another example, the polar additive is ditetrahydrofurfurylpropane, triethylamine or tetramethylethylenediamine.

The polar additive may be for example used in an amount of 0.001 to 50 g, 0.001 to 10 g, 0.005 to 1 g, or 0.005 to 0.1 g, based on 100 g in total of the added monomer.

In another example, the polar additive may be used in an amount of 0.001 to 10 g, 0.005 to 1 g, or 0.005 to 0.1 g, based on 1 mmol in total of the added organometallic compound.

When the conjugated diene monomer and the aromatic vinyl monomer are copolymerized, a block copolymer may be generally prepared due to difference in reaction speed between the monomers. However, when the polar additive is added, reaction speed of the vinyl aromatic compound which has a low reaction speed is increased, microstructure of the copolymer corresponding thereto, for example, random copolymer is advantageously induced.

The polymerization (a) may be for example anionic polymerization.

In another example, the polymerization (a) may be living anionic polymerization for obtaining active ends by growth reaction by anions.

The polymerization (a) may be for example polymerization at an elevated temperature or polymerization at a fixed temperature.

The polymerization at an elevated temperature means a polymerization method which includes elevating a reaction temperature by heating after adding an organometallic compound. The polymerization at a fixed temperature means a polymerization method which does not include heating after adding an organometallic compound.

A temperature of the polymerization (a) is for example −20 to 200° C., 0 to 150° C. or 10 to 120° C.

In the modification (b), for example, one or more types, or two or three types of the compound represented by Formula 1 may be added.

In addition, the modification (b) may include reaction, for example, at 0 to 90° C. for one minute to 5 hours.

The method for preparing a modified conjugated diene polymer according to the present invention may be, for example, batch or continuous polymerization including one, two or more reactors.

The modified conjugated diene polymer may be, for example, prepared according to the method for preparing a modified conjugated diene polymer.

The modified conjugated diene polymer rubber composition according to the present invention comprises 0.1 to 200 parts by weight of an inorganic filler with respect to 100 parts by weight of the modified conjugated diene polymer.

The modified conjugated diene polymer rubber composition may further include, for example, another conjugated diene polymer.

The another conjugated diene polymer may be, for example, styrene-butadiene rubber (SBR), butadiene rubber (BR), natural rubber or a mixture thereof.

The SBR may be, for example, a solution styrene-butadiene rubber (SSBR).

The modified conjugated diene polymer rubber composition according to the present invention may, for example, include 20 to 100 parts by weight of the modified conjugated diene polymer and 0 to 80 parts by weight of the another conjugated diene polymer.

In another example, the modified conjugated diene polymer rubber composition may include 20 to 99 parts by weight of the modified conjugated diene polymer and 1 to 80 parts by weight of the another conjugated diene polymer.

In another example, the modified conjugated diene polymer rubber composition may include 10 to 100 parts by weight of the modified conjugated diene polymer, 0 to 90 parts by weight of the another conjugated diene polymer, 0 to 100 parts by weight of carbon black, 5 to 200 parts by weight of silica and 2 to 20 parts by weight of a silane coupling agent.

In another example, the modified conjugated diene polymer rubber composition may include 10 to 100 parts by weight of the modified conjugated diene polymer, 0 to 90 parts by weight of the another conjugated diene polymer, 0 to 100 parts by weight of carbon black, 5 to 200 parts by weight of silica and 2 to 20 parts by weight of a silane coupling agent, wherein a total weight of the modified conjugated diene polymer and the another conjugated diene polymer is 100 parts by weight.

In another example, the modified conjugated diene polymer rubber composition according to the present invention is prepared by mixing 100 parts by weight of a polymer mixture including 10 to 99% by weight of the modified conjugated diene polymer and 1 to 90% by weight of the another conjugated diene polymer with 1 to 100 parts by weight of carbon black, 5 to 200 parts by weight of silica and 2 to 20 parts by weight of a silane coupling agent.

The inorganic filler may be present in an amount of, for example, 10 to 150 parts by weight, or 50 to 100 parts by weight.

The inorganic filler may be, for example, carbon black, a silica filler or a mixture thereof.

In another example, the inorganic filler may be silica. In this case, advantageously, dispersibility is greatly improved and hysteresis loss is greatly decreased because silica particles are bonded to (capped to) an end of the modified conjugated diene polymer.

The modified conjugated diene polymer rubber composition may for example further include 1 to 100 parts by weight of an oil.

The oil may be, for example, a mineral oil, a softening agent or the like.

The oil may be for example used in an amount of 10 to 100 parts by weight or 20 to 80 parts by weight, with respect to 100 parts by weight of the conjugated diene copolymer. Within this range, there are advantages in that properties are efficiently exhibited, the rubber composition is suitably softened and processability is thus excellent.

The modified conjugated diene polymer rubber composition may be for example used as a material for tires or tire treads.

The tire may be produced from a material containing the modified conjugated diene polymer rubber composition.

The modifying agent according to the present invention is represented by the following Formula 2:

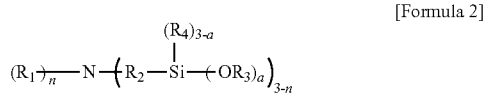

[Formula 2]

wherein $R_1$ is an alkyl group or an alkylsilyl group, $R_2$ is an alkyl group or an alkylene group, $R_3$ and $R_4$ are an alkyl group, a is an integer of 1 to 3, and n is an integer of 0 to 2, wherein two $R_1$ bonded to nitrogen may be identical or different when n is 2, and similarly, corresponding groups may be identical or different when 3-n is 2 or more.

Hereinafter, preferred examples will be provided for better understanding of the present invention. These examples are only provided to illustrate the present invention and it will be apparent to those skilled in the art that various modifications and alterations are possible within the scope and technical range of the present invention. Such modifications and alterations fall within the scope of claims included herein.

EXAMPLE

Example 1

260 g of styrene, 720 g of 1,3-butadiene, 5,000 g of normal hexane, and 1.3 g of 2,2-bis(2-oxolanyl)propane as a polar additive were added to a 20 L autoclave reactor and an inner temperature of the reactor was elevated to 40° C. When the inner temperature of the reactor reached 40° C., 4 mmol of n-butyl lithium was added to the reactor and an adiabatic temperature-rising reaction was proceeded until the reaction was stabilized. 20 minutes after the adiabatic temperature-rising reaction was finished, 20 g of 1,3-butadiene was added to the reactor. After 5 minutes, 5 mmol of bis(methyldimethoxysilylpropyl)-N-methylamine was added to the reactor and reaction was proceeded for 15 minutes. Then, polymerization reaction was stopped using ethanol and 5 ml of a 0.3 wt % solution of butylated hydroxytoluene (BHT) as an antioxidant in hexane was then added to the reaction mixture.

The polymerization product was added to warm water heated by steam, the mixture was stirred, the solvent was removed, and the resulting solution was then roll-dried to remove the residual solvent and water, thereby producing a modified conjugated diene polymer. Analysis results of the modified conjugated diene polymer thus produced are shown in the following Table 1.

Example 2

A modified conjugated diene polymer was prepared in the same manner as in Example 1, except that 0.8 g of 2,2-bis(2-oxolanyl)propane was added as a polar additive. Analysis results of the modified conjugated diene polymer are shown in the following Table 1.

Example 3

A modified conjugated diene polymer was prepared in the same manner as in Example 2, except that bis(trimethoxysilylpropyl)-N-methylamine was used as a modifying agent, instead of bis(methyldimethoxysilylpropyl)-N-methylamine. Analysis results of the modified conjugated diene polymer are shown in the following Table 1.

Example 4

A modified conjugated diene polymer was prepared in the same manner as in Example 1, except that diethylaminopropyl trimethoxysilane was used, instead of bis(methyldimethoxysilylpropyl)-N-methylamine. Analysis results of the modified conjugated diene polymer are shown in the following Table 1.

Comparative Example 1

Analysis results of an unmodified conjugated diene polymer (5025-2HM, produced by Lanxess Deutschland Gmbh) which is the most commonly sold are shown in the following Table 1.

Comparative Example 2

A modified conjugated diene polymer was prepared in the same manner as in Example 2, except that 1.2 mmol of dimethyldichlorosilane as a coupling agent was added, instead of bis(methyldimethoxysilylpropyl)-N-methylamine as a modifying agent. Analysis results of the modified conjugated diene polymer are shown in Table 1.

Analysis of conjugated diene polymers prepared in Examples 1 to 4 and Comparative Examples 1 to 2 was performed in accordance with the following method.

a) Mooney viscosity: two specimens having a weight of 15 g or more were pre-heated for one minute using MV-2000 produced by ALPHA Technologies and Mooney viscosity thereof was measured at 100° C. for 4 minutes.

b) Styrene monomer (SM) and vinyl content: measured using NMR.

c) Weight average molecular weight (Mw), number average molecular weight (Mn) and molecular weight distribution (PDI): measured by GPC at 40° C. At this time, a combination of two pieces of PLgel Olexis columns produced by Polymer Laboratories and one piece of PLgel mixed-C column was used as a column. All newly replaced columns were mixed bed-type columns. In addition, polystyrene (PS) was used as a GPC standard material for determination of molecular weight.

TABLE 1

| Type | | Examples | | | | Comparative Examples | |
|---|---|---|---|---|---|---|---|
| | | 1 | 2 | 3 | 4 | 1 | 2 |
| Sample | | A | B | C | D | E | F |
| n-butyllithium (mmol) | | 4 | 4 | 4 | 4 | — | 4 |
| Polar additive (g) | | 1.3 | 0.8 | 0.8 | 1.3 | | 0.8 |
| Modifying agent (mmol) | a | 12 | 12 | — | — | — | — |
| | b | — | — | — | 12 | — | — |
| | c | — | — | 12 | — | — | — |
| Coupling agent | d | — | — | — | — | — | 1.2 |
| TDAE oil | phr | — | — | — | — | 37.5 | — |
| Mooney viscosity (MV) | | 54 | 74 | 70 | 50 | 61 | 66 |
| NMR (%) | SM | 26 | 26 | 26 | 26 | 26 | 26 |
| | Vinyl | 50 | 44 | 45 | 47 | 50 | 44 |
| GPC (×10⁴) | Mn | 30 | 32 | 25 | 30 | 39 | 31 |
| | Mw | 49 | 39 | 33 | 50 | 69 | 37 |
| | PDI | 1.6 | 1.2 | 1.3 | 1.7 | 1.8 | 1.2 | a: bis(methyldimethoxysilylpropyl)-N-methylamine
b: diethylaminopropyltrimethoxysilane
c: bis(trimethoxysilylpropyl)-N-methylamine
d: dimethyldichlorosilane

TABLE 2

| (Unit: parts by weight) | S-1 | S-2 |
|---|---|---|
| Rubber | 100.0 | 137.5 |
| Silica | 70.0 | 70.0 |
| Coupling agent | 11.02 | 11.2 |
| Oil | 33.75 | — |
| Zinc | 3.0 | 3.0 |
| Stearic acid | 2.0 | 2.0 |
| Antioxidant | 2.0 | 2.0 |
| Anti-aging agent | 2.0 | 2.0 |
| Wax | 1.0 | — |
| Rubber accelerator | 1.75 | 1.75 |
| Sulfur | 1.5 | 1.5 |
| Vulcanization accelerator | 2.0 | 2.0 |
| Total weight | 230.2 | 234.0 |

A, B, C, D, E and F among samples shown in Table 1 were used as rubber raw materials and were mixed under mixing conditions shown in the following Table 3 to prepare conjugated diene polymer rubber compositions. A, B, C, D and F were mixed under mixing conditions of S-1 and E was mixed under mixing conditions of S-2.

The mixing of the rubber compositions of the conjugated diene polymer was performed using a Banbury mixer equipped with a temperature controller as follows. In primary mixing, a rubber raw material (conjugated diene polymer), a filler, an organosilane coupling agent, an oil, zinc, a stearic acid antioxidant, an anti-aging agent, a wax and accelerators were primarily mixed at 80 rpm. At this time, the temperature of the mixer was controlled and a primary mixture was obtained at a discharge temperature of 140 to 150° C. In secondary mixing, after the primary mixture was cooled to room temperature, a rubber, sulfur and a vulcanization accelerator were added to a mixer and a secondary mixture was obtained at a discharge temperature of 45 to 60° C. In tertiary mixing, the secondary mixture was molded and was vulcanized using a vulcanization press at 180° C. for T90+10 minutes to prepare a vulcanized rubber.

Physical properties of the prepared vulcanized rubbers were measured in accordance with the following method.

1) Tensile Strength Test

Tensile strength at break and tensile strength at an elongation of 300% (300% modulus) of specimens were measured by tensile strength testing in accordance with ASTM 412.

2) Viscoelasticity

A dynamic mechanical analyzer produced by TA Instrument was used. Tan δ was measured while varying strain in a torsional mode at a frequency of 10 Hz at different measurement temperatures of 0 to 60° C. Payne effect was indicated as a difference between a minimum and a maximum at a strain of 0.2% to 40%. As payne effect decreases, dispersibility of filler such as silica is improved. As Tan δ at a low temperature of 0° C. increases, resistance on wet roads is improved, and as Tan δ at a high temperature of 60° C. decreases, hysteresis loss is low, and rolling resistance, that is, fuel consumption, of tires, is reduced. Physical properties of vulcanized rubbers are shown in Table 3.

TABLE 3

| Item | Example 5 | Example 6 | Example 7 | Example 8 | Comparative Example 3 | Comparative Example 4 |
|---|---|---|---|---|---|---|
| Sample | A | B | C | D | E | F |
| 300% modulus (Kgf/cm²) | 123 | 123 | 130 | 108 | 98 | 104 |
| Tensile strength (Kgf/cm²) | 184 | 188 | 167 | 162 | 161 | 168 |
| Tan δ at 0° C. | 0.986 | 0.851 | 0.881 | 0.881 | 0.547 | 0.542 |
| Tan δ at 60° C. | 0.075 | 0.066 | 0.080 | 0.085 | 0.085 | 0.098 |
| ΔG' at 60° C. (payne effect) | 0.34 | 0.35 | 0.35 | 0.38 | 0.56 | 0.74 |

As can be seen from Table 3 above, the modified conjugated diene polymer rubber compositions according to Examples 5 to 8 exhibited a great increase in 300% modulus (tensile strength) and tensile strength, and a high Tan δ at 0° C., as compared to Comparative Examples 3 and 4, which indicates that tires comprising the modified conjugated diene polymer according to the present invention exhibited superior resistance on wet roads.

In addition, the modified conjugated diene polymers of Examples 5 to 8 exhibited a low Tan δ at 60° C., as compared to Comparative Examples 3 and 4. Tires comprising the modified conjugated diene polymer according to the present invention exhibited low rolling resistance as compared to the prior art.

In addition, the modified conjugated diene rubber copolymers of Examples 5 to 8 according to the present invention exhibited considerably low ΔG' at 60° C., as compared to Comparative Examples 3 and 4, which indicates that dispersibility of silica is greatly improved.

What is claimed is:

1. A method for preparing a modified conjugated diene polymer comprising:
   (a) polymerizing a conjugated diene monomer, or a conjugated diene monomer and an aromatic vinyl monomer in the presence of a solvent using an organometallic compound to prepare an active polymer having a metal end group; and
   (b) adding a compound represented by the following Formula 2 to the active polymer to modify the active polymer:

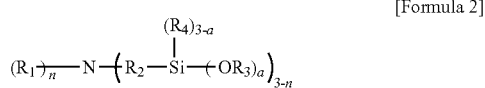
[Formula 2]

wherein $R_1$ is an alkyl group, $R_2$ is an alkylene group, $R_3$ and $R_4$ are an alkyl group, a is an integer of 1 to 3, n is 1, and $R_1$, $R_3$ and $R_4$ are identical or different.

2. The method according to claim 1, wherein the organometallic compound is used in an amount of 0.01 to 10 mmol, based on 100 g in total of the monomer.

3. The method according to claim 1, wherein a molar ratio of the organometallic compound and the compound represented by Formula 2 is 1:0.1 to 1:10.

4. The method according to claim 1, wherein the polymerizing (a) further comprises adding a polar additive.

5. The method according to claim 4, wherein the polar additive is added in an amount of 0.001 to 50 g, based on 1 mmol in total of the organometallic compound.

6. A modified conjugated diene polymer rubber composition comprising 0.1 to 200 parts by weight of an inorganic filler with respect to 100 parts by weight of a modified conjugated diene polymer, wherein the modified conjugated diene polymer is represented by the following Formula 1:

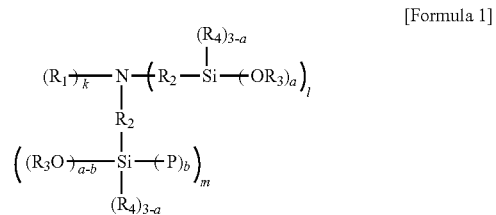
[Formula 1]

wherein $R_1$ is an alkyl group, $R_2$ is an alkylene group, $R_3$ and $R_4$ are an alkyl group, a is an integer of 1 to 3, l and k are 1, m is 1, p is a conjugated diene polymer chain, and b is an integer of 1 to 3, wherein b is not greater than a.

7. The modified conjugated diene polymer rubber composition according to claim 6, wherein the composition comprises 0 to 100 parts by weight of carbon black, 5 to 200 parts by weight of silica and 2 to 20 parts by weight of a silane coupling agent, with respect to 100 parts by weight of a polymer mixture comprising 10 to 100% by weight of the modified conjugated diene polymer and 0 to 90% by weight of another conjugated diene polymer.

8. The modified conjugated diene polymer rubber composition according to claim 6, wherein the inorganic filler is a silica filler.

9. A tire comprising the modified conjugated diene polymer rubber composition according to claim 6.

10. A modifying agent comprising a compound represented by the following Formula 2:

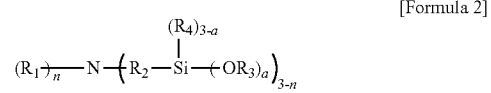
[Formula 2]

wherein $R_1$ is an alkyl group, $R_2$ is an alkylene group, $R_3$ and $R_4$ are an alkyl group, a is an integer of 1 to 3, n is 1, and $R_1$, $R_3$ and $R_4$ are identical or different.

* * * * *